(12) United States Patent
Komiya et al.

(10) Patent No.: US 9,233,181 B2
(45) Date of Patent: Jan. 12, 2016

(54) ENDOSCOPE CLEANING/DISINFECTING APPARATUS

(71) Applicant: OLYMPUS MEDICAL SYSTEMS CORP., Tokyo (JP)

(72) Inventors: Takaaki Komiya, Hachioji (JP); Jiro Komiya, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/598,289

(22) Filed: Jan. 16, 2015

(65) Prior Publication Data

US 2015/0125350 A1  May 7, 2015

Related U.S. Application Data

(63) Continuation of application No. PCT/JP2013/084107, filed on Dec. 19, 2013.

(30) Foreign Application Priority Data

Dec. 26, 2012  (JP) .................................. 2012-283228

(51) Int. Cl.
| | |
|---|---|
| A61L 2/18 | (2006.01) |
| G02B 23/24 | (2006.01) |
| A61B 1/00 | (2006.01) |
| A61B 1/12 | (2006.01) |
| A61L 2/24 | (2006.01) |
| B08B 9/032 | (2006.01) |

(52) U.S. Cl.
CPC ............. *A61L 2/186* (2013.01); *A61B 1/00057* (2013.01); *A61B 1/123* (2013.01); *A61B 1/125* (2013.01); *A61L 2/24* (2013.01); *B08B 9/0325* (2013.01); *G02B 23/24* (2013.01); *A61L 2202/24* (2013.01)

(58) Field of Classification Search
CPC ............. A61L 2/16; A61L 2/18; A61L 2/186; A61L 2/24; A61L 2202/24; B08B 9/0325; G02B 23/24
See application file for complete search history.

(56) References Cited

U.S. PATENT DOCUMENTS

| 2005/0065405 A1* | 3/2005 | Hasegawa ...................... 600/158 |
| 2010/0022839 A1* | 1/2010 | Onishi et al. ................... 600/158 |
| 2012/0211033 A1 | 8/2012 | Onishi et al. |

FOREIGN PATENT DOCUMENTS

| EP | 2 478 828 A1 | 7/2012 |
| JP | 11-113840 A | 4/1999 |
| JP | 2002-345749 A | 12/2002 |
| WO | WO 2004/049925 A1 | 6/2004 |
| WO | WO 2012/035982 A1 | 3/2012 |

OTHER PUBLICATIONS

International Search Report dated Mar. 18, 2014 issued in PCT/JP2013/084107.

* cited by examiner

*Primary Examiner* — Timothy Cleveland
(74) *Attorney, Agent, or Firm* — Scully, Scott, Murphy & Presser, P.C.

(57) ABSTRACT

Endoscope connection portions, a fluid feeding duct, a liquid supply duct, a pump, a first atmospheric exposure duct including one end connected to the fluid feeding duct and the other end exposed to atmosphere, a relief valve disposed at an intermediate position of the first atmospheric exposure duct, a first stop section disposed at an intermediate position of the first atmospheric exposure duct, and a control section that performs control to supply a liquid to ducts of endoscopes and controls at least opening/closing operation of the first stop section are included.

13 Claims, 2 Drawing Sheets

ENDOSCOPE CLEANING/DISINFECTING APPARATUS

CROSS REFERENCE TO RELATED APPLICATION

This application is a continuation application of PCT/JP2013/084107 filed on Dec. 19, 2013 and claims benefit of Japanese Application No. 2012-283228 filed in Japan on Dec. 26, 2012, the entire contents of which are incorporated herein by this reference.

BACKGROUND OF INVENTION

1. Field of the Invention

The present invention relates to an endoscope cleaning/disinfecting apparatus that cleans/disinfects an endoscope.

2. Description of the Related Art

An endoscope cleaning/disinfecting apparatus configuration in which an endoscope duct is connected to an endoscope connection portion of an endoscope cleaning/disinfecting apparatus and a liquid is supplied from a liquid supply source into the endoscope duct via a liquid supply duct, a fluid feeding duct and the endoscope connection portion inside the endoscope cleaning/disinfecting apparatus, thereby cleaning/disinfecting the inside of the endoscope duct is well known.

Also, a configuration in which in order to detect clogging of an endoscope duct, for example, a flow measurement section that measures a flow of a liquid passing through a fluid feeding duct is provided in a fluid feeding duct is also well known.

Here, when clogging occurs in the endoscope duct, if the liquid is continuously fed into the endoscope duct, the pressure inside the endoscope duct becomes equal to or exceeds a withstanding pressure, resulting in breakage of the endoscope duct.

Therefore, International Publication No. WO2004-049925 discloses a configuration in which an atmospheric exposure duct is connected to the downstream side of a fluid feeding duct and a relief valve that opens under a pressure that is equal to or exceeds a set pressure set to be lower than a withstanding pressure of an endoscope duct is provided in the atmospheric exposure duct. As a result of the relief valve being opened, a liquid and a gas are let out from the fluid feeding duct via the atmospheric exposure duct, whereby the pressure inside the endoscope duct is made to be lower than the withstanding pressure.

Therefore, when detection of clogging of an endoscope duct is performed using a flow measurement section, normally, clogging of the endoscope duct is detected as a result of a measurement value from the flow measurement section decreasing or becoming zero.

SUMMARY OF THE INVENTION

An endoscope cleaning/disinfecting apparatus according to an aspect of the present invention is an endoscope cleaning/disinfecting apparatus for cleaning/disinfecting an endoscope, the apparatus including: an endoscope connection portion connected to a duct of the endoscope; a fluid feeding duct including one end connected to the endoscope connection portion; a liquid supply duct connecting the fluid feeding duct and a liquid supply source; a first atmospheric exposure duct including one end connected to the fluid feeding duct and another end exposed to atmosphere; a relief valve disposed at an intermediate position of the first atmospheric exposure duct, the relief value opening under a set pressure; a first stop section disposed at an intermediate position of the first atmospheric exposure duct, the first stop section opening or closing the first atmospheric exposure duct; and a control section that performs control to supply a liquid into the duct of the endoscope via the liquid supply duct, the fluid feeding duct and the endoscope connection portion and controls at least opening/closing operation of the first stop section.

Also, an endoscope cleaning/disinfecting apparatus according to another aspect of the present invention is an endoscope cleaning/disinfecting apparatus for cleaning/disinfecting an endoscope, the apparatus including: an endoscope connection portion connected to a duct of the endoscope; a fluid feeding duct including one end connected to the endoscope connection portion; a liquid supply duct including one end connected to another end of the fluid feeding duct, and another end connected to the liquid supply source; a pump provided in the liquid supply duct, the pump making a liquid stored in the liquid supply source flow from the other end of the liquid supply duct toward the endoscope connection portion; a first atmospheric exposure duct including one end connected to the fluid feeding duct, and another end exposed to atmosphere; a relief valve disposed at an intermediate position of the first atmospheric exposure duct, the relief valve opening upon application of a pressure that is equal to or exceeds a predetermined pressure from the one end toward the other end of the first atmospheric exposure duct; a first stop section disposed at an intermediate position of the first atmospheric exposure duct, the first stop section opening/closing the first atmospheric exposure duct; and a control section that controls driving of the pump and opening/closing of the first stop section, the control section closing the first stop section and driving the pump to supply the liquid into the duct of the endoscope.

DETAILED DESCRIPTION OF THE PREFERRED EMBODIMENT(S)

An embodiment of the present invention will be described below with reference to the drawings.

Figure 1:
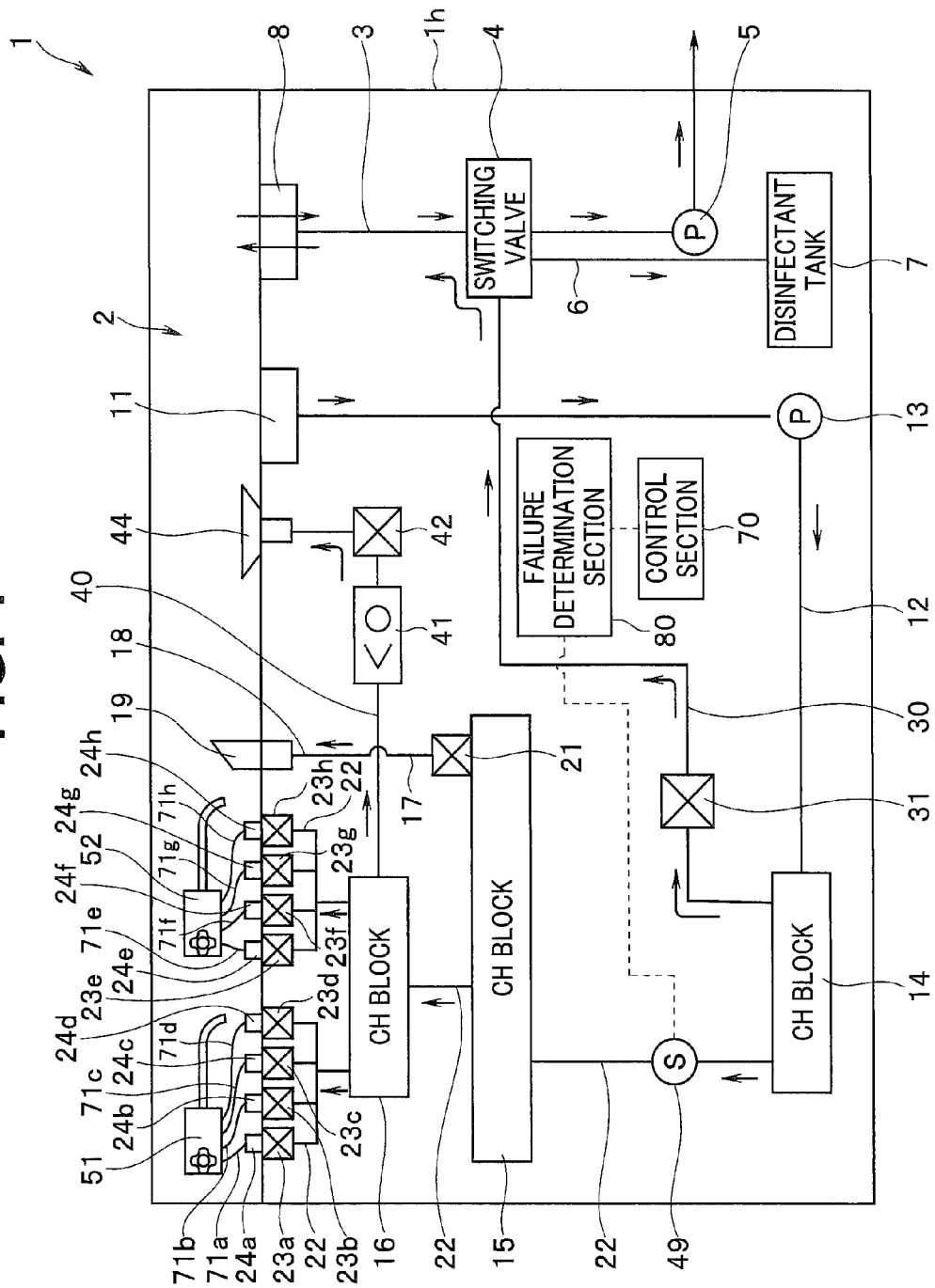
FIG. 1 is a block diagram schematically illustrating a configuration for performing endoscope clogging detection in an endoscope cleaning/disinfecting apparatus.

FIG. 1 is a block diagram schematically illustrating a configuration for performing endoscope clogging detection in an endoscope cleaning/disinfecting apparatus.

Note that FIG. 1 illustrates a configuration for cleaning/disinfecting two endoscopes using an endoscope cleaning/disinfecting apparatus as an example. However, it should be understood that the number of endoscopes that can be cleaned/disinfected using an endoscope cleaning/disinfecting apparatus is not limited to two.

As illustrated in FIG. 1, an endoscope cleaning/disinfecting apparatus 1 used to clean/disinfect outer surfaces of endoscopes 51 and 52 and the insides of ducts included in the respective endoscopes 51 and 52 includes a cleaning/disinfecting bath 2 capable of receiving the endoscopes 51 and 52 in an apparatus body 1h.

Also, at respective positions of the apparatus body 1h that face the cleaning/disinfecting bath 2, endoscope connection portions 24a, 24b, 24c and 24d, which are to be connected to ducts of the endoscope 51 via tubes 71a, 71b, 71c and 71d, are provided. Note that the number of endoscope connection portions to be connected to the ducts of the endoscope 51 is not limited to four.

Likewise, at respective positions of the apparatus body 1h that faces the cleaning/disinfecting bath 2, endoscope connection portions 24e, 24f, 24g and 24h, which are to be connected to the ducts of the endoscope 52 via tubes 71e, 71f, 71g and 71h, are provided. Note that the number of endoscope connection portions to be connected to the ducts of the endoscope 52 is also not limited to four.

Furthermore, a third stop section 23a that closes or opens the endoscope connection portion 24a is provided at the endoscope connection portion 24a, a third stop section 23b that closes or opens the endoscope connection portion 24b is provided at the endoscope connection portion 24b. Also, a third stop section 23c that closes or opens the endoscope connection portion 24c is provided at the endoscope connection portion 24c, and a third stop section 23d that closes or opens the endoscope connection portion 24d is provided at the endoscope connection portion 24d.

Therefore, along with opening/closing of the third stop sections 23a to 23d, switching between supply and interruption of supply of a liquid into the ducts of the endoscope 51 via the tubes 71a to 71d is performed. Note that examples of the liquid include e.g., a cleaning solution, a disinfectant, alcohol, rinse water and a gas-liquid two-phase fluid including a mixture of a gas phase and a liquid phase.

Likewise, a third stop section 23e that closes or opens the endoscope connection portion 24e is provided at the endoscope connection portion 24e, and a third stop section 23f that closes or opens the endoscope connection portion 24f is provided at the endoscope connection portion 24f. Also, a third stop section 23g that closes or opens the endoscope connection portion 24g is provided at the endoscope connection portion 24g, and a third stop section 23h that closes or opens the endoscope connection portion 24h is provided at the endoscope connection portion 24h.

Therefore, along with opening/closing of the third stop sections 23e to 23h, switching between supply and interruption of supply of the liquid into the ducts of the endoscope 52 via the tubes 71e to 71h is performed.

Each of the third stop sections 23a to 23h includes, for example, a solenoid valve that can be opened/closed. Also, opening/closing operation of each of the third stop sections 23a to 23h is controlled by a later-described control section 70 provided inside the apparatus body 1h.

Also, inside the apparatus body 1h, a fluid feeding duct 22 including one end connected to the respective endoscope connection portions 24a to 24h is provided. Note that a CH (channel) block 14 is provided at the other end of the fluid feeding duct 22, and a flow measurement section 49 is disposed at an intermediate position of the fluid feeding duct 22. Furthermore, if the CH block 14 is positioned upstream of the fluid feeding duct 22, the flow measurement section 49, a CH block 15 and a CH block 16 are disposed in the fluid feeding duct 22 in this order from the upstream side.

Inside the apparatus body 1h, one end of a liquid supply duct 12 is connected to the CH block 14. Note that the other end of the liquid supply duct 12 is connected to a circulation port 11 provided in the cleaning/disinfecting bath 2. Also, at an intermediate position of the liquid supply duct 12, a channel pump 13, which is to be driven by means of operation control performed by the later-described control section 70, is disposed.

Also, inside the apparatus body 1h, one end of a second atmospheric exposure duct 30 is connected to a position between the flow measurement section 49 in the fluid feeding duct 22 and the other end of the fluid feeding duct 22, for example, the CH block 14.

The other end of the second atmospheric exposure duct 30 is connected to a later-described switching valve 4, and is exposed to atmosphere in the cleaning/disinfecting bath 2 via a later-described drain duct 3 and a drain port 8. Note that at an intermediate position of the second atmospheric exposure duct 30, a second stop section 31 that closes or opens the second atmospheric exposure duct is provided.

Note that the second stop section 31 includes, for example, a solenoid valve that can be opened/closed. Also, opening/closing operation of the second stop section 31 is controlled by the later-described control section 70 provided inside the apparatus body 1h.

If a pressure inside the fluid feeding duct 22 and the liquid supply duct 12 is high, the channel pump 13 that is being halted and a non-illustrated compressor fail to restart. Therefore, the second stop section 31 is intended to let pressure out from the drain port 8 via the second atmospheric exposure duct 30 and the drain duct 3 before driving of the channel pump 13 and the compressor, in order to prevent the pressure inside the fluid feeding duct 22 and the liquid supply duct 12 from becoming equal to or exceeding a predetermined pressure.

Note that the second stop section 31 is controlled by the later-described control section 70 so that the second stop section 31 is opened before driving of the channel pump 13 and the compressor for the purposes of detection of clogging of the ducts of the endoscopes 51 and 52, which will be described later, and detection of failure of a first stop section 42, which will be described later, and is closed in cases other than the predetermined purposes.

This is because, if the second stop section 31 is opened when the liquid is supplied from the endoscope connection portions 24a to 24h in the ducts of the endoscopes 51 and 52 in a cleaning/disinfecting process, pressure for feeding the liquid into the ducts of the endoscopes 51 and 52 decreases.

Also, inside the apparatus body 1h, the switching valve 4 is disposed at an intermediate position of the drain duct 3 including one end connected to the drain port 8 provided in the cleaning/disinfecting bath 2. Note that the other end of the drain duct 3 is positioned outside the apparatus body 1h. Also, in the drain duct 3, a drain pump 5, which is to be driven by operation control performed by the later-described control section 70, is disposed between the other end of the drain duct 3 and the switching valve 4.

Also, one end of a disinfectant duct 6 is connected to a disinfectant tank 7, and the other end of the disinfectant duct 6 is connected to the switching valve 4.

The switching valve 4 is a valve for switching between draining of a liquid drained from the cleaning/disinfecting bath 2 via the drain port 8 and the drain duct 3 as a result of driving of the drain pump 5 to the outside of the apparatus body 1h from the other end of the drain duct 3 and collection of the liquid to the disinfectant tank 7 via the disinfectant duct 6 where the liquid is a disinfectant, the switching being made by operation control performed by the later-described control section 70.

The flow measurement section 49 is intended to measure a flow of liquid passing through the fluid feeding duct 22, and includes, for example, a known flowmeter.

Also, inside the apparatus body 1h, one end of a water supply circulation duct 17 is connected to the CH block 15 via a pump valve 21, opening/closing of which is controlled by the later-described control section 70. Also, the other end of the water supply circulation duct 17 is connected to a pump valve nozzle 19 provided at a position facing the cleaning/disinfecting bath 2 in the apparatus body 1h.

The pump valve nozzle 19 is intended to supply a liquid in the cleaning/disinfecting bath 2 again to the cleaning/disinfecting bath 2 via the circulation port 11, the liquid supply duct 12, the fluid feeding duct 22 and the water supply circulation duct 17 as a result of driving of the channel pump 13, thereby measuring a flow rate of the pump.

Also, inside the apparatus body 1h, one end of a first atmospheric exposure duct 40 is connected to a position between the one end of the fluid feeding duct 22 and the flow measurement section 49, for example, the CH block 16 in the fluid feeding duct 22.

The other end of the first atmospheric exposure duct 40 is connected to a cleaning case 44 provided in the cleaning/disinfecting bath 2 and is thereby exposed to atmosphere via the cleaning case 44. The cleaning case 44 is intended to receive, e.g., buttons removed from the endoscopes 51 and 52. Note that the other end of the first atmospheric exposure duct 40 does not necessarily need to be connected to the cleaning case 44 and may simply be exposed inside the cleaning/disinfecting bath 2.

Also, inside the apparatus body 1h, at respective intermediate positions of the first atmospheric exposure duct 40, a relief valve 41 that opens under a set pressure, and the first stop section 42 that closes or opens the first atmospheric exposure duct 40 are disposed.

The first stop section 42 includes, for example, a solenoid valve that can be opened/closed. Also, opening/closing operation of the first stop section 42 is controlled by the later-described control section 70 provided inside the apparatus body 1h.

Furthermore, the first stop section 42 is controlled by the later-described control section 70 so that the first stop section 42 is closed to push out liquid stored in the endoscope at a single burst when detection of clogging of the ducts of the endoscopes 51 and 52 is performed and when detection of failure of the first stop section 42 is performed. In other words, in a process of cleaning/disinfecting the insides of the ducts of the endoscopes 51 and 52, which is performed by supplying a liquid to the ducts via the endoscope connection portions 24a to 24h, the first stop section 42 is opened.

The relief valve 41 opens upon application of a pressure that is equal to or exceeds a predetermined pressure from the one end to the other end of the first atmospheric exposure duct. In other words, in a process of cleaning/disinfecting the insides of the ducts the endoscopes 51 and 52, which is performed by supplying liquid into the ducts via the endoscope connection portions 24a to 24h, if clogging exists in the ducts, the relief valve 41 opens under the set pressure, thereby letting pressure inside the fluid feeding duct 22 and the liquid supply duct 12 out to the cleaning/disinfecting bath 2 together with the liquid via the first atmospheric exposure duct 40.

Note that the set pressure under which the relief valve 41 starts opening is set to be smaller than a pressure inside the fluid feeding duct 22 and the liquid supply duct 12 when the channel pump 13 is driven to supply liquid in the cleaning/disinfecting bath 2 to the ducts of the endoscopes 51 and 52 from the endoscope connection portions 24a to 24h via the circulation port 11, the liquid supply duct 12 and the fluid feeding duct 22 in a state in which the first stop section 42 is opened and the second stop section 31 is closed and all of the ducts of the endoscopes 51 and 52 are clogged (hereinafter referred to as "duct close-off pressure").

Also, in the first atmospheric exposure duct 40, the relief valve 41 is disposed on the fluid feeding duct 22 side, that is, the upstream side relative to the first stop section 42. This is because provision of the relief valve 41 on the upstream side relative to the first stop section 42 provides a smaller difference in the close-off pressure between liquid and gas when the close-off pressure is set based on liquid compared to that of a case where the relief valve 41 is provided on the downstream side.

Note that the duct close-off pressure in the duct is a value smaller than a withstanding pressure of the ducts of the endoscopes 51 and 52, and, for example, if the withstanding pressure of the ducts of the endoscopes 51 and 52 is 0.2 MPa, the duct close-off pressure is a value that is smaller than 0.2 MPa, for example, 0.18 MPa. Therefore, the set pressure under which the relief valve 41 starts opening is smaller than 0.18 MPa, for example, 0.12 MPa.

In other words, the relief valve 41 is configured so that, when a liquid is supplied into the ducts of the endoscopes 51 and 52 in a normal cleaning/disinfecting process, even if all of the ducts are clogged, the relief valve 41 reliably starts opening before the ducts are broken, and the close-off pressure becomes equal to or smaller than a pressure that is equal to or exceeds the withstanding pressure of the ducts.

Note that the withstanding pressure of the ducts of the endoscopes 51 and 52, the duct close-off pressure in the ducts and the set pressure under which the relief valve 41 starts opening are not limited to 0.2 MPa, 0.18 MPa and 0.12 MPa, respectively.

For the relief valve, there are no specific limitations, but it is preferable to use a diaphragm valve. The diaphragm valve is advantageous not only in that the diaphragm valve is not frozen up by, e.g., a chemical passing through the atmospheric exposure duct, but also in that the diaphragm valve enables provision of a large flow with a small size. However, a diaphragm valve is largely affected by hardening/softening of resin, and thus, effects resulting from application of the present invention are large.

The control section 70 is provided inside the apparatus body 1h, and is intended to perform opening/closing control of a valve of the drain port 8, the pump valve 21, the first stop section 42, the second stop section 31 and the third stop sections 23a to 23h, also perform switching control of the switching valve 4 and further performs driving control of the drain pump 5 and the channel pump 13.

Therefore, when the third stop sections 23a to 23h and the first stop section 42 are opened and the valve of the drain port 8, the pump valve 21 and the second stop section 31 are closed, and the channel pump 13 is driven, by the control section 70, the liquid in the cleaning/disinfecting bath 2 is supplied into the ducts of the endoscopes 51 and 52 via the circulation port 11, the liquid supply duct 12, the fluid feeding duct 22, the endoscope connection portions 24a to 24h and the tubes 71a to 71h. In other words, the control section 70 performs control to supply the liquid into the ducts of the endoscopes 51 and 52. Therefore, in the present embodiment, the cleaning/disinfecting bath 2 provides a liquid supply source.

In this case, the relief valve 41 starts opening when the pressure inside the fluid feeding duct 22 and the liquid supply duct 12 reaches a predetermined pressure, for example, 0.12 MPa or more, and thereby lets pressure inside the ducts out together with the liquid to the cleaning/disinfecting bath 2 via the first atmospheric exposure duct 40.

Consequently, in cases other than clogging detection, even though all of the ducts of the endoscopes 51 and 52 are clogged, the relief valve 41 opens before the withstanding pressure of the ducts, 2.0 MPa, is reached, preventing breakage of the ducts of the endoscopes 51 and 52.

Note that the control section 70 performs the above-described control when liquid is continuously fed into the ducts of the endoscopes 51 and 52 to clean the insides of the ducts.

Also, when liquid is intermittently fed into the ducts of the endoscopes 51 and 52 to clean the insides of the ducts, for example, when a known gas-liquid two-phase fluid is supplied to clean the insides of the ducts, the control section 70 performs control to close the first stop section 42 in addition to the above-described control; thereby supplying the liquid intensively from the endoscope connection portions 24a to 24h only into the ducts of the endoscopes 51 and 52.

Also, if the control section 70 performs control to close the first stop valve and the third stop valves and open the second stop valve and the pump valve 21, the liquid is supplied from the pump valve nozzle 19 to the cleaning/disinfecting bath 2 via the water supply circulation duct 17.

In other words, the flow rate of the pump can be measured by the flow measurement section. As a result of the measurement of the flow rate of the pump, a threshold value for determining whether or not the endoscope ducts are clogged can be changed. This is because, since if the flow rate of the pump is large, the flow when an endoscope ducts are clogged is also large, it is necessary to change the threshold value according to the flow rate of the pump.

Also, when the first stop section 42 is opened and the second stop section 31, the third stop sections 23a to 23h, the valve of the drain port 8 and the pump valve 21 are closed and the channel pump 13 is driven by the control section 70, the liquid in the cleaning/disinfecting bath 2 is supplied only to the cleaning case 44 via the circulation port 11, the liquid supply duct 12, the fluid feeding duct 22 and the first atmospheric exposure duct 40.

Note that according to a normal cleaning/disinfecting program in the cleaning/disinfecting apparatus 1, supply of liquid only to the first atmospheric exposure duct 40 is performed at a rate of once per several seconds during a process of supply of the liquid into the ducts of the endoscopes 51 and 52 via the endoscope connection portions 24a to 24h.

Also, when the valve of the drain port 8 is opened, the switching valve 4 is switched to the drain duct 3 side and the drain pump 5 is driven by the control section 70, the liquid in the cleaning/disinfecting bath 2 is drained to the outside of the apparatus body 1h via the drain port 8 and the drain duct 3.

In this case, if the liquid is a disinfectant, when the switching valve 4 is switched to the disinfectant duct 6 side by the control section 70, the disinfectant in the cleaning/disinfecting bath 2 is collected to the disinfectant tank 7 via the drain port 8, the drain duct 3 and the disinfectant duct 6.

Next, operation of the present embodiment, more specifically, operation of the control section 70 in detection of clogging of the ducts of the endoscopes 51 and 52 will be described.

When detection of clogging of the ducts of the endoscopes 51 and 52 is performed, first, the control section 70 performs control to close the first stop section 42 and also performs control to open the second stop section 31.

Subsequently, the control section 70 performs control to sequentially open only one of the third stop sections 23a to 23h and also performs control to drive the channel pump 13, and then, liquid in the cleaning/disinfecting bath 2 is supplied into the ducts of the endoscopes 51 and 52 via the circulation port 11, the liquid supply duct 12, the fluid feeding duct 22, the endoscope connection portions 24a to 24h and the tubes 71a to 71h.

Subsequently, if at least one of the ducts of the endoscopes 51 and 52 is clogged, the pressure inside the fluid feeding duct 22 and the liquid supply duct 12 becomes high, but, as a result of the second stop section 31 being opened, the pressure is let out together with the liquid to the cleaning/disinfecting bath 2 via the second atmospheric exposure duct 30, the drain duct 3 and the drain port 8 on the upstream side relative to the flow measurement section 49.

Note that as described above, the pressure inside the fluid feeding duct 22 and the liquid supply duct 12 in this case is smaller than the withstanding pressure of the ducts of the endoscopes 51 and 52, and thus, the ducts of the endoscopes 51 and 52 are not broken.

Also, since the first stop section 42 is closed, even if the relief valve 41 is opened as a result of clogging of the ducts of the endoscopes 51 and 52, the pressure inside the fluid feeding duct 22 and the liquid supply duct 12 is not let out from the first atmospheric exposure duct 40, but is let out together with the liquid via the second atmospheric exposure duct 30.

Here, as described above, although the pressure under which the relief valve 41 opens varies depending on the water temperature, the second stop section 31 is a valve that is opened by the operation control performed by the control section 70, and thus, the pressure inside the fluid feeding duct 22 and the liquid supply duct 12 is let out together with the liquid via the second atmospheric exposure duct 30 irrespective of the water temperature.

Also, even if the liquid is let out from the second atmospheric exposure duct 30 as a result of at least one of the ducts of the endoscopes 51 and 52 being clogged, the first stop section 42 being closed and the second stop section 31 being opened, the one end of the second atmospheric exposure duct 30 is connected to the CH block 14, that is, to the upstream side of the flow measurement section 49, and thus, when at least one of the ducts of the endoscopes 51 and 52 is clogged, the flow of the liquid measured by the flow measurement section 49 is definitely smaller than that of a case where none of the ducts of the endoscopes 51 and 52 is clogged. Thus, the endoscope duct clogging can correctly be detected. This is a reason that the one end of the second atmospheric exposure duct 30 is connected to the upstream side relative to the flow measurement section 49.

In other words, if the one end of the second atmospheric exposure duct 30 is connected to the downstream side relative to the flow measurement section 49, when at least one of the ducts of the endoscopes 51 and 52 is clogged, the liquid flows into the second atmospheric exposure duct 30 in which the second stop section 31 is open, a measurement value from the flow measurement section 49 does not change, resulting in failure to perform correct clogging detection. This becomes more pronounced as the ducts of the endoscopes 51 and 52 have small diameters.

Here, a failure determination section 80 can easily detect failure of the first stop section 42 using the fact that the set pressure under which the relief valve 41 opens is set to be smaller than the aforementioned duct close-off pressure as described above.

The failure determination section 80 is connected to the control section 70 and the flow measurement section 49. The failure determination section 80 can detect that the first stop section is not opened/closed according to the control performed by the control section 70, that is, failure of the first stop section, by comparing a result of measurement by the flow measurement section 49 with a reference value in consideration of the state of the opening/closing control of the first stop section, the second stop section and the third stop section by the control section 70.

More specifically, first, where it is detected that the first stop section 42 fails as it is closed, that is, the first stop section 42 is unable to open, the control section 70 performs control to close the second stop section 31, the third stop sections 23a to 23h and the pump valve 21, and also performs control to open a valve of the circulation port 11 and the first stop section 42, and subsequently performs control to drive the channel pump 13.

In this case, the failure determination section 80 can easily detect that the first stop section 42 remains closed in despite of the control to open the first stop section 42 being performed, by detecting an abnormal pressure inside the fluid feeding duct 22 and the liquid supply duct 12, and thus, can easily detect that the first stop section 42 fails as it is closed. It should be understood that if no abnormal pressure is detected, the liquid flows in the first atmospheric exposure duct 40, the failure determination section 80 can easily detect that the first stop section 42 is open.

Next, when it is detected that the first stop section 42 fails as it is opened, that is, the first stop section 42 is unable to be closed, the control section 70 performs control to close the pump valve 21 and the third stop sections 23a to 23h. Furthermore, the control section 70 performs control to open the second stop section 31 and performs control to close the first stop section 42, and subsequently performs control to drive the channel pump 13.

Here, if the first stop section 42 is closed according to the operation control performed by the control section 70, the entire liquid flows to the second atmospheric exposure duct 30 side because the one end of the second atmospheric exposure duct 30 is connected to the upstream side relative to the flow measurement section 49, and the measurement value provided by the flow measurement section 49 is not varied, and thus, the closing of the first stop section 42 can easily be detected.

On the other hand, if the first stop section 42 is not closed but remains open, since the relief valve 41 is opened by a pressure that is smaller than the close-off pressure of a case where only the second stop section 31 is opened, the liquid flows into the first atmospheric exposure duct 40, resulting in variation in the measurement value provided by the flow measurement section 49, and thus, failure of the first stop section 42 as it remains open can easily be detected.

As described above, the control section 70 can easily detect failure of the first stop section 42, which is closed by the control performed by the control section 70 when clogging of the ducts of the endoscopes 51 and 52 is detected.

As described above, in the present embodiment, it has been described that when detection of clogging of the ducts of the endoscopes 51 and 52 is performed, the control section 70 performs control to close the first stop section 42 and performs control to open the second stop section 31.

It has also been described that the first atmospheric exposure duct 40 is connected to the downstream side of the flow measurement section 49 in the fluid feeding duct 22, and the second atmospheric exposure duct 30 is connected to the upstream side relative to the flow measurement section 49 in the fluid feeding duct 22.

According to the above, if at least one of the ducts of the endoscopes 51 and 52 is clogged, no liquid flows to the first atmospheric exposure duct 40 connected to the downstream side of the flow measurement section 49 because the first stop section 42 is closed. Consequently, even if the ducts of the endoscopes 51 and 52 have small diameters, the flow rate of liquid measured by the flow measurement section 49 definitely decreases as a result of duct clogging, enabling correct detection of the duct clogging in the endoscopes 51 and 52.

Also, if the ducts of the endoscopes 51 and 52 are clogged, the pressure inside the fluid feeding duct 22 and the liquid supply duct 12 increases, but since the second stop section 31 is opened, the pressure is let out together with the liquid from the second atmospheric exposure duct 30, preventing breakage of the ducts of the endoscopes 51 and 52.

Furthermore, since the second stop section 31 is opened by the control performed by the control section 70, the pressure can reliably be let out irrespective of the water temperature.

According to the above, the endoscope cleaning/disinfecting apparatus 1 having a configuration that enables high-accurate detection of clogging of an endoscope duct without breakage of the endoscope duct can be provided.

Note that although the present embodiment has been described in terms of the case where two endoscopes 51 and 51 are received in the cleaning/disinfecting bath 2 and cleaned/disinfected and the case where detection of clogging of the ducts of two endoscopes 51 and 52 is performed as examples, it should be understood that the number of endoscopes is not limited to two.

Note that the endoscope cleaning/disinfecting apparatus may include a gas supply duct connected to a gas supply source, the gas supply duct introducing a gas supplied from the gas supply source to endoscopes connected to endoscope connection portions.

The gas supply duct may be connected to any of the endoscope connection portions 24a to 24h, any of the CH block 14, the CH block 15 and the CH block 16, the liquid supply duct 12 or the fluid feeding duct.

The gas supply source may be included in the endoscope cleaning/disinfecting apparatus as a component thereof, or the gas supply source may be attached/detached to/from the endoscope cleaning/disinfecting apparatus by means of external connection.

The control section can make dirt in the endoscopes be pushed out by driving the liquid supply source to fill the endoscopes with a liquid, and then closing the first stop section, the second stop section and the pump valve, and driving the gas supply source to introduce a gas to the endoscopes. In this case, as a result of the first stop section being closed, the gas can be introduced to the endoscopes with a high pressure maintained, enabling the liquid charged in the endoscopes to be pushed out with strong force.

Figure 2:
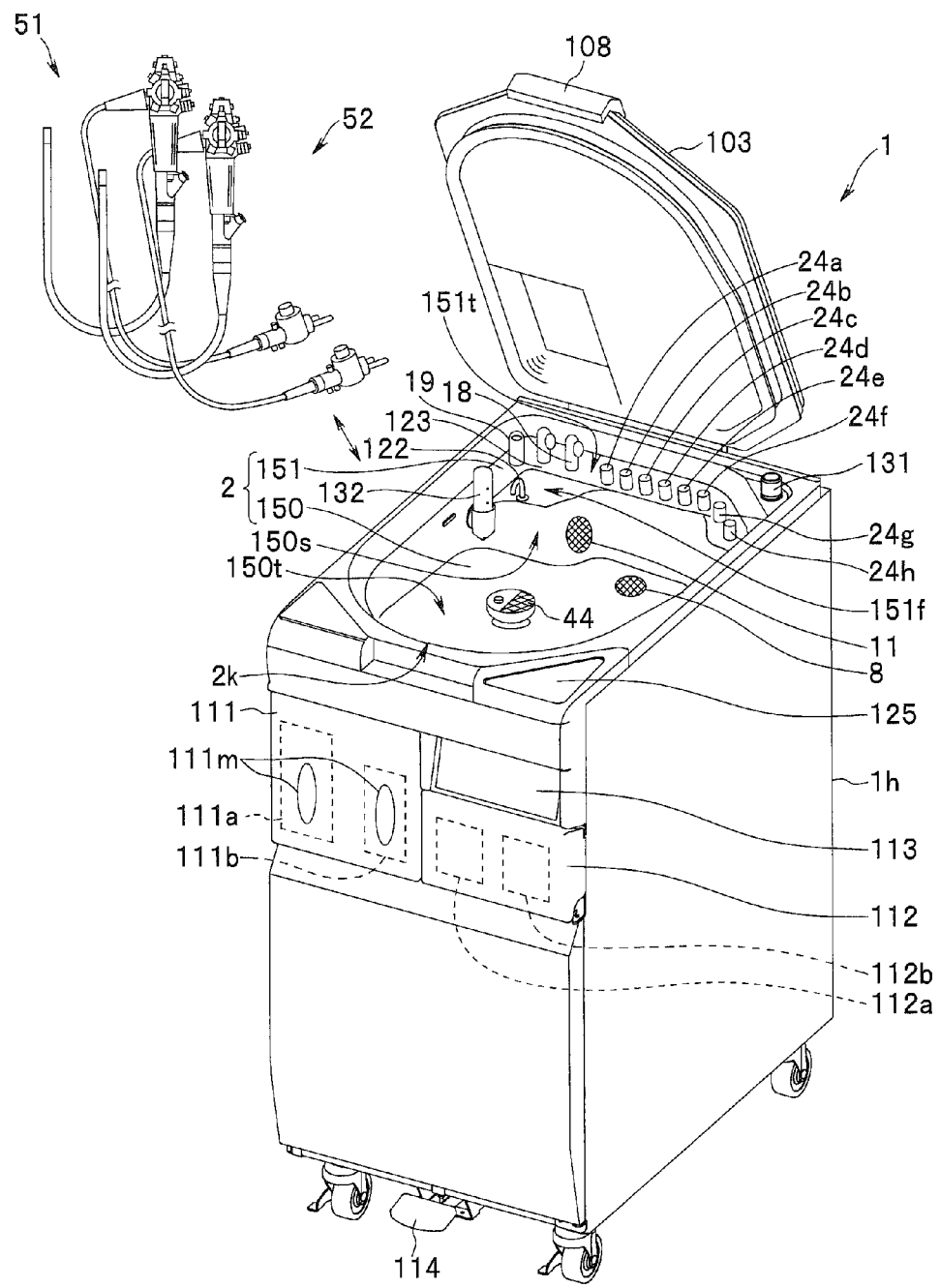
FIG. 2 is a perspective diagram illustrating an example of an endoscope cleaning/disinfecting apparatus including the endoscope duct clogging detection configuration in FIG. 1 in an apparatus body.

Note that an example of an endoscope cleaning/disinfecting apparatus having the above-described configuration in the apparatus body 1h is illustrated in FIG. 2. FIG. 2 is a perspective diagram illustrating an example of an endoscope cleaning/disinfecting apparatus having the endoscope duct clogging detection configuration in FIG. 1 in an apparatus body thereof.

As illustrated in FIG. 2, an endoscope cleaning/disinfecting apparatus 1 is an apparatus that cleans/disinfects two endoscopes 51 and 52 simultaneously, and a main part of the endoscope cleaning/disinfecting apparatus 1 includes an apparatus body 1h, and a top cover 103 on an upper portion thereof, the top cover 103 being a lid body connected to the apparatus body 1h, via, for example, a non-illustrated hinge in such a manner that the top cover 103 can be opened/closed.

Note that in a state in which the top cover 103 is closed on the apparatus body 1h, the apparatus body 1h and the top cover 103 are closed and locked via, for example, a latch 108 arranged over positions of the apparatus body 1h and the top cover 103 that face each other.

Also, in, for example, an upper portion of a left part portion of a front face of the apparatus body 1h in the Figure, which is close to an operator, a detergent/alcohol tray 111 is arranged in such a manner that the detergent/alcohol tray 111 can be drawn forward from the apparatus body 1h.

The detergent/alcohol tray 111 accommodates a tank 111a with a detergent charged therein, the detergent being a liquid used when the endoscopes 51 and 52 are cleaned/disinfected, and a tank 111b with an alcohol charged therein, the alcohol being a liquid used when the cleaned/disinfected endoscopes 51 and 52 are dried, and as a result of the detergent/alcohol tray 111 being able to be drawn out, a predetermined liquid can be charged in each of the tanks 111a and 111b.

Note that the detergent charged in the tank 111a is a concentrated detergent, which is to be diluted to a predetermined concentration by tap water subjected to filtration treatment by a non-illustrated water supply filter.

Also, window portions 111m are provided in the detergent/alcohol tray 111, and the operator can check remaining amounts of the detergent and the alcohol charged in the respective tanks 111a and 111 b through the respective window portions 111m.

Also, in, for example, an upper portion of a right half portion of the front face of the apparatus body 1h, a cassette tray 112 is arranged in such a manner that the cassette tray 112 can be drawn forward from the apparatus body 1h. The cassette tray 112 accommodates a bottle 112a with a main agent such as acetyl hydroperoxide charged therein, the main agent being used to provide a disinfectant, which is a liquid used for disinfecting the endoscopes 51 and 52, and a bottle 112b with a buffer for the main agent charged therein, and as a result of the cassette tray 112 being able to be drawn out, a predetermined liquid can be supplied to each of the bottles 112a and 112b. Note that a mixture of the main agent and the buffer is referred to as a disinfectant.

Furthermore, in a portion above the cassette tray 112 in the front face of the apparatus body 1h, a sub-operation panel 113 with, e.g., a cleaning/disinfecting time period display and an instruction button for heating the disinfectant arranged thereon is arranged.

Also, a pedal switch 114 for opening the top cover 103 closed on the upper portion of the apparatus body 1h upward from the apparatus body 1h by a stepping operation by the operator is arranged in a lower portion of the front face of the apparatus body 1h in the Figure.

Also, a main operation panel 125 with a start switch for cleaning/disinfecting operation of the apparatus body 1h and setting switches such as a cleaning/disinfecting mode selection switch arranged therein is provided, for example, close to a right edge in the Figure on the front face side of an upper face of the apparatus body 1h, which is close to the operator.

Also, a water supply hose connection port 131 for supply tap water to the apparatus body 1h, to which a water supply hose connected to a tap water faucet is connected, is arranged on the back side of the upper face of the apparatus body 1h, which faces the front face close to the operator. Note that a mesh filter that filtrates tap water may be arranged in the water supply hose connection port 131.

Furthermore, a cleaning/disinfecting bath 2 capable of receiving the endoscopes 51 and 52, which is open upward and is opened/closed by the top cover 103, is provided in a roughly-center portion of the upper face of the apparatus body 1h.

The cleaning/disinfecting bath 2 includes, for example, a bath body 150, and a terrace portion 151 continuously provided at an outer circumference of an endoscope receiving opening of the bath body 150.

When used endoscopes 51 and 52 are cleaned/disinfected, the bath body 150 can receive the endoscopes 51 and 52, and in a bottom face 150t, which is a surface inside the bath of the bath body 150, a drain port 8 for draining, e.g., a cleaning solution, water or a disinfectant, which is a liquid supplied to the bath body 150, from the bath body 150 is provided.

Also, at an arbitrary position in a peripheral side face 150s, which is a surface inside the bath of the bath body 150, a circulation port 11 for supplying, e.g., the cleaning solution, the water or the disinfectant supplied in the bath body 150 to the respective ducts arranged inside the endoscopes 51 and 52 from the bath body 150 and supplying the liquid again from a water supply circulation nozzle 18 to the bath body 150 is provided. Note that the circulation port 11 may be provided with a filter that filtrates, e.g., the cleaning solution, the water or the disinfectant. Note that the circulation port 11 may be provided in the bottom face 150t of the bath body 150.

Also, in a rough center of the bottom face 150t of the bath body 150, a cleaning case 44 for receiving, e.g., buttons and the like such as respective scope switches and forceps plugs of the endoscopes 51 and 52 and cleaning/disinfecting, e.g., the buttons and the like and the forceps plugs together with the endoscopes 51 and 52 is arranged.

At an arbitrary position in the side face 150s of the bath body 150, a covered water level sensor 132 for detecting a level of the liquid such as cleaning solution, the water or the disinfectant supplied to the bath body 150 and reliably supplying the liquid up to a set level in the cleaning/disinfecting bath 2 is provided.

The terrace portion 151 of the cleaning/disinfecting bath 2 includes an inclined surface oriented diagonally upward, more specifically, a circumferential terrace surface 151t inclined at a prescribed angle relative to, for example, the bottom face 150t of the bath body 150.

In a face other than the terrace surface 151t of the terrace portion 151, that is, a parallel face 151f, which is parallel to the bottom face 150t of the bath body 150, a detergent nozzle 122 for supplying the cleaning solution from the detergent tank 111a to the bath body 150 is arranged. Note that the detergent nozzle 122 may be provided in the terrace surface 151t.

Also, in the terrace surface 151t of the terrace portion 151, a disinfectant nozzle 123 for supplying a disinfectant from a non-illustrated chemical tank to the bath body 150 is arranged.

Furthermore, in the terrace surface 151t, the water supply circulation nozzle 18 for supplying water used for cleaning or rinsing to the bath body 150 or supplying, e.g., the cleaning solution, the water or the disinfectant sucked from the circulation port 11 of the bath body 150 again to the bath body 150 is arranged. Note that the disinfectant nozzle 123 and the water supply circulation nozzle 18 may be provided in the parallel face 151f.

Also, on the side of the terrace surface 151t of the terrace portion 151 that faces an operation position 2k for the operator, endoscope connection portions 24a to 24h that supply a fluid into the ducts of the endoscopes 51 and 52 are provided.

What is claimed is:

1. An endoscope cleaning/disinfecting apparatus for cleaning/disinfecting an endoscope, the apparatus comprising:
    an endoscope connection portion connected to a duct of the endoscope;
    a fluid feeding duct including one end connected to the endoscope connection portion;
    a liquid supply duct connecting the fluid feeding duct and a liquid supply source;
    a pump provided in the liquid supply duct, the pump making the liquid stored in the liquid supply source flow from the other end of the liquid supply duct toward the endoscope connection portion;
    a first atmospheric exposure duct including one end connected to the fluid feeding duct and another end exposed to atmosphere;

a relief valve disposed at a first intermediate position of the first atmospheric exposure duct, the relief valve opening upon application of a pressure that is equal to or exceeds a predetermined pressure from the one end toward the other end of the first atmospheric exposure duct;

a first stop section disposed at a second intermediate position of the first atmospheric exposure duct, the first stop section opening/closing the first atmospheric exposure duct; and a control section that controls driving of the pump and opening/closing of the first stop section, and when detection of clogging of the duct of the endoscope is performed, closes the first stop section and drives the pump to supply the liquid into the duct of the endoscope.

2. The endoscope cleaning/disinfecting apparatus according to claim 1, wherein the fluid feeding duct is provided with a flow measurement section.

3. The endoscope cleaning/disinfecting apparatus according to claim 2, wherein the one end of the first atmospheric exposure duct is connected between the flow measurement section and the one end of the fluid feeding duct in the fluid feeding duct.

4. The endoscope cleaning/disinfecting apparatus according to claim 3, wherein in the first atmospheric exposure duct, the first intermediate position where the relief valve is disposed is closer to the fluid feeding duct than the second intermediate position where the first stop section is disposed.

5. The endoscope cleaning/disinfecting apparatus according to claim 2, further comprising a second atmospheric exposure duct including one end connected to the fluid feeding duct between the flow measurement section and the other end of the fluid feeding duct, and another end exposed to atmosphere.

6. The endoscope cleaning/disinfecting apparatus according to claim 5, wherein
a second stop section that opens/closes the second atmospheric exposure duct is disposed at an intermediate position of the second atmospheric exposure duct, and
the control section further controls opening/closing operation of the second stop section.

7. The endoscope cleaning/disinfecting apparatus according to claim 6,
wherein when detection of clogging of the inside of the duct of the endoscope is performed using the flow measurement section,
the control section performs control to close the first stop section and performs control to open the second stop section, and performs control to drive the pump to supply the liquid into the duct of the endoscope.

8. The endoscope cleaning/disinfecting apparatus according to claim 7, wherein the set pressure under which the relief valve opens is smaller than a pressure inside the fluid feeding duct when the liquid is supplied into the duct of the endoscope by the control section in a state in which the first stop section is opened, the second stop section is closed and the duct of the endoscope is clogged.

9. The endoscope cleaning/disinfecting apparatus according to claim 8, wherein
the endoscope connection portion includes a third stop section that opens/closes the endoscope connection portion, and the control section further controls opening/closing operation of the third stop section, and
if the control section detects that the first stop section fails to open, the control section performs control to supply the liquid into the first atmospheric exposure duct in a state in which the second stop section and the third stop section are closed and the first stop section is opened.

10. The endoscope cleaning/disinfecting apparatus according to claim 8, wherein
the endoscope connection portion includes a third stop section that closes or opens the endoscope connection portion, and the control section controls opening/closing operation of the third stop section, and
when detecting whether or not the first stop section fails to be closed, the control section performs control to supply the liquid into the first atmospheric exposure duct in a state in which the third stop section is closed, the second stop section is opened and the first stop section is closed.

11. The endoscope cleaning/disinfecting apparatus according to claim 9, wherein
if the liquid is intermittently fed from the fluid feeding duct into the duct of the endoscope via the endoscope connection portion to clean the duct, the control section performs control to open the third stop section and close the first stop section and the second stop section, and
if the liquid is continuously fed from the fluid feeding duct into the duct of the endoscope via the endoscope connection portion to clean the duct, the control section performs control to open the first stop section and the third stop section, and close the second stop section.

12. The endoscope cleaning/disinfecting apparatus according to claim 1, comprising a gas supply duct including one end that is in communication with the endoscope connection portion, and another end connected to a gas supply source, the gas supply duct being controlled by the control section,
wherein the control section closes the first stop section, and introduces the gas from the gas supply source to the endoscope in a state in which a liquid is charged in the endoscope as a result of driving of the pump.

13. The endoscope cleaning/disinfecting apparatus according to claim 1, wherein the relief valve is a diaphragm valve.

* * * * *